(12) United States Patent
Feldon et al.

(10) Patent No.: US 7,802,884 B2
(45) Date of Patent: Sep. 28, 2010

(54) COMPACT OCULAR FUNDUS CAMERA

(75) Inventors: Steven Feldon, Rochester, NY (US);
Geunyoung Yoon, Pittsford, NY (US)

(73) Assignee: University of Rochester, Rochester, NY (US)

( * ) Notice: Subject to any disclaimer, the term of this patent is extended or adjusted under 35 U.S.C. 154(b) by 122 days.

(21) Appl. No.: 11/864,766

(22) Filed: Sep. 28, 2007

(65) Prior Publication Data
US 2008/0231803 A1 Sep. 25, 2008

Related U.S. Application Data

(60) Provisional application No. 60/847,669, filed on Sep. 28, 2006.

(51) Int. Cl.
*A61B 3/14* (2006.01)
*A61B 3/00* (2006.01)

(52) U.S. Cl. .................. 351/206; 351/246; 351/219; 396/18

(58) Field of Classification Search ............. 351/206, 351/205, 246, 219; 396/6, 18, 543, 335, 396/360, 366
See application file for complete search history.

(56) References Cited

U.S. PATENT DOCUMENTS

| | | | |
|---|---|---|---|
| 4,023,189 A | 5/1977 | Govignon | |
| 5,943,116 A | 8/1999 | Zeimer | |
| 6,019,472 A * | 2/2000 | Koester et al. | 351/219 |
| 6,142,630 A * | 11/2000 | Koester | 351/219 |
| 6,321,038 B1 | 11/2001 | Kudoh | |

* cited by examiner

*Primary Examiner*—Darryl J Collins
*Assistant Examiner*—Zachary Wilkes
(74) *Attorney, Agent, or Firm*—James W. Hill; McDermott Will & Emery LLP

(57) ABSTRACT

Embodiments of a compact camera for imaging the ocular fundus are described. In some embodiments, the camera is a light, handheld camera that acquires a plurality of images of the fundus. The camera can be configured to acquire images manually or automatically. A movable imaging lens or movable image detector provides the images in a series to obtain an image with optimal focus. The camera can acquire a series of images and allow selection of an optimal image either manually, or automatically. In some embodiments, the camera is part of an imaging system that includes a base station. The base station exchanges data with the camera and can receive image data generated by the image detector of the camera. The base can further include networking capability, such that image data can be distributed over a network or to other communication or computing devices.

30 Claims, 5 Drawing Sheets

COMPACT OCULAR FUNDUS CAMERA

RELATED APPLICATIONS

This application claims priority to U.S. provisional application 60/847,669, filed Sep. 28, 2006, the entire contents of which are herein incorporated by reference.

FIELD OF THE INVENTIONS

Embodiments of the disclosure are useful in the area of medical imaging apparatus, particularly in the area of apparatus for use in imaging a fundus of an eye.

BACKGROUND OF THE INVENTIONS

Screening for eye diseases has become increasingly important as the population ages in the United States and around the world. Major causes of irreversible blindness include diabetic retinopathy, macular degeneration, and glaucoma. Standard screening measures such as visual acuity testing or intraocular pressure measurement are inadequate, since these tests only identify patients late in the disease process.

Despite such limitations, there is increasing pressure to screen patients for early indicators of eye disease. For example, health maintenance organizations and governments encourage annual screening of diabetics for retinopathy. As macular degeneration can be effectively prevented or slowed by treatment with multivitamins, early detection is advantageous. It is also well-established that cupping of the optic disc is the prelude to devastating visual loss in glaucoma.

Traditionally, eye examinations have been performed using an ophthalmoscope. More recently, camera systems have been developed to image the interior of the eye. In a traditional fundus camera, the ocular fundus is illuminated by a beam of light that is projected through the pupil and onto the retina. Light reflected back from the retina is directed to an observation microscope and/or camera for observation or recording. An eye care professional is then able to review the recorded images for signs of eye disease.

SUMMARY OF THE INVENTIONS

Optimal outcomes in the treatment of most, if not all, eye diseases lies in early diagnosis. Early diagnosis can only be made via detailed examination of the ocular fundus. One way in which to examine the fundus is by use of the direct ophthalmoscope. Unfortunately, ophthalmoscopy is technically very demanding, especially with an undilated pupil, the usual condition when screening for eye disease. Probably fewer than 10% of non-ophthalmologists or non-optometrists can effectively examine an eye using the direct ophthalmoscope. In addition, the direct ophthalmoscope has a very high magnification and small field of view, so that identifying disease processes may be problematic even to the trained practitioner. Further, the traditional ophthalmoscope does not provide a way to record images, and thus, it is not possible to perform accurate follow up of disease progression over a period of time, other than by references to a practitioner's notes or recollections.

In order to address the need for early diagnosis of eye disease in the screening setting, there has been increasing emphasis on imaging technologies, such as non-mydriatic fundus cameras with or without telemedicine applications software. Ocular fundus cameras have been developed that avoid some of the problems inherent with the use of an ophthalmoscope. Some examples include U.S. Pat. No. 4,238, 142 to Richards et al., which discloses aligning an instrument for photographing the ocular fundus by using a physical aperture designed to permit illumination of only a small area of the optic disc; U.S. Pat. No. 4,579,430 to Bille, which discloses an apparatus wherein a laser beam scans across the retina and directs reflected light to a photoelectric receiver to generate a television image; U.S. Pat. No. 4,854,691 to Sekine et al., which discloses a laser beam scanning type fundus camera with first and second light receiving portions for receiving laser light reflected by the eye fundus and for guiding a fluorescence light excited at the eye fundus and an electronic circuit for forming an image of an eye fundus on a television monitor; U.S. Pat. No. 5,225,859 to Fleischman, which discloses a combined apparatus for the capture, processing, and archival recording of digital or analog images of the ocular and retinal anatomy by indirect ophthalmoscopy and fluorescence angiography; U.S. Pat. No. 5,745,163 to Nakamura et al., which discloses an apparatus that includes an ocular fundus camera and a CCD for converting light components into image signals; U.S. Pat. No. 5,943,116 to Zeimer, which discloses a system for obtaining images of the fundus of an eye that includes an illumination device which directs a light beam onto a portion of the fundus of an eye and a video camera which records the portion of the light reflected from the fundus of the eye. Another example is a fundus camera dedicated to screening diabetic retinopathy in a primary care physician's office, as described by Zeimer et al., in *Investigative Ophthalmology and Visual Science*, 43: 1581-1587 (2002). All of the foregoing references are herein incorporated by reference in their entireties.

Photo documentation solves many issues, including accurate observation and verifiable diagnosis. A problem with existing devices, however, is that they tend to be expensive (e.g., $20,000 or more), and require considerable technical expertise to operate. Moreover, current fundus camera apparatus are large pieces of equipment and, as such, are generally not portable. As a result, fundus photography as a screening tool has been implemented only to a very limited extent, usually in large multi-specialty practices. Thus, the widespread implementation of fundus photography, or the use in remote areas or areas underserved by eye care professionals, has so far not been practical.

Because of the limitations in methods of diagnostic screening for eye disease, it may be advantageous to provide early diagnostic screening for potentially blinding diseases using a low magnification, large field of view, non-mydriatic fundus camera, that preserves the benefits of accurate observation and verifiable diagnosis. It may be further advantageous to provide a device that is compact, relatively low-cost, and requires little expertise or training to operate. It may further be advantageous to replace the installation and use of direct ophthalmoscopes with such a device. It may also be advantageous to have a camera that takes advantage of digital imaging technology to produce images suitable for electronic transmission or storage.

Some embodiments described herein provide a compact hand-held camera for imaging a fundus of an eye with an imaging detector configured to acquire an image of the fundus. The image detector can be a CCD or CMOS chip that provides a digital image output. The camera has a contact member at one end of the housing, configured to contact the cornea of the eye and transmit light reflected from the fundus to the image detector. The camera further comprises an illumination source for illumination of the fundus. The camera can include an imaging lens that focuses the image of the fundus on the image detector.

Thus, in some embodiments, there is provided a compact ocular fundus camera, for imaging at least a portion of a fundus of an eye, comprising: a contact member, positioned at a distal end of the camera, a portion of the contact member being configured to contact at least a portion of a cornea of the eye, and wherein the contact member is substantially transparent to light; an image detector module, located proximally with respect to the contact member, the image detector module being configured to acquire an image of at least a portion of the fundus and output data relating to the fundus; an imaging lens, positioned between the contact member and the image detector module, the image lens directing the image to the image detector module; and a power supply that provides power to the image detector module.

In some embodiments, there is provided a compact ocular fundus camera system, for imaging at least a portion of a fundus of an eye, including a camera comprising having a camera housing with proximal and distal ends; a contact member, positioned at or distal to a distal end of the camera housing, a portion of the contact member being configured to contact at least a portion of a cornea of the eye, and wherein the contact member is substantially transmissive of light; an image detector module, located proximally with respect to the contact member, the image detector module being configured to acquire an image of at least a portion of the fundus and to output data indicative of the image; and an imaging lens, positioned between the contact member and the image detector module, the image lens directing the image to the image detector module. The image detector module and the imaging lens are coupled to the camera housing; and at least one of the image detector module and the imaging lens is movable substantially along an optical axis of the camera housing.

In some embodiments, at least one of the image detector module and the imaging lens is moved within the camera housing by at least one of a release of potential energy that is stored in a biasing member coupled to the camera housing, electromagnetic energy, and a manually applied force.

In some embodiments, at least one of the image detector module and the imaging lens is moved within the camera housing by a release of potential energy that is stored in a biasing member coupled to the camera housing, and further comprising an operator-activated switch configured to release of at least a portion of the potential energy.

In some embodiments, the manually applied force is transferred by an operator to at least one of the image detector module and the imaging lens by a lever extending outside the camera housing.

In some embodiments, the camera system further includes a plurality of contact points, and wherein the image detector module is configured to acquire a plurality of images based on a relative position of the plurality of contact points with respect to at least one of the image detector module and the imaging lens.

In some embodiments, the imaging lens is movable with respect to the contact member. In some embodiments, the camera housing is elongate and is less than about 15 cm in its longest dimension. In certain embodiments, the camera housing is elongate and is less than about 10 cm in its longest dimension. In some embodiments, the system includes a base station that exchanges data with the camera and stores the outputted data indicative of the image. In some embodiments, the contact member is configured to conform substantially to an anterior surface of the cornea when the contact member contacts the cornea.

In some embodiments, the imaging lens is movable with respect to the image detector module during acquisition of images by the image detector module. In some embodiments, the imaging lens is movable substantially along an optical axis of the camera. In some embodiments, the image detector module is movable with respect to the contact member during acquisition of images by the image detector module.

In some embodiments, the imaging lens comprises a single element lens. In some embodiments, the imaging lens comprises a multi-element lens.

In some embodiments, the portion of the contact member that contacts the cornea comprises a substantially concave portion. In some embodiments, the concave portion of the contact member comprises a radius of curvature substantially equal to a radius of curvature of the cornea of the eye that the contact member contacts. In some embodiments, the concave portion of the contact member has a radius of curvature that matches the radius of curvature of the cornea within a range of error from about 0% to about 30%.

In some embodiments, the contact member is configured to substantially conform to the radius of curvature of the cornea when the contact member contacts the cornea. In some embodiments, the contact member further comprises a transparent coverlet. In some embodiments, the contact member has a refractive index substantially equal to that of the cornea.

In some embodiments, the camera further comprises at least one illumination source coupled to the camera. In some embodiments, the at least one illumination source emits one of ultra-violet (UV), visible, and infrared light. In some embodiments, the at least one illumination source comprises a light-emitting diode (LED). In some embodiments, light from the at least one illumination source is directed towards the eye by an optical fiber.

In some embodiments, the camera further comprises a control module that controls image acquisition by the image detector.

In some embodiments, the camera further comprises a data transmission module that exchanges information between the camera and at least one device peripheral to the camera. In some embodiments, the data transmission module further comprises at least one of a data transmission cable and a wireless transceiver.

In some embodiments, the camera further comprises a memory module that stores the data relating to the fundus.

In some embodiments, the power supply comprises at least one of a disposable battery and a rechargeable battery.

In some embodiments, there is provided a fundus camera imaging system comprising: a compact ocular fundus camera that is configured to image at least a portion of a fundus of an eye, the camera comprising: a contact member, located at a distal end of the camera, configured to contact at least a portion of a cornea of the eye, the contact member being substantially transparent to light; an image detector module, located proximal the contact member, configured to acquire an image of at least a portion of the fundus and output data of the acquired image; an imaging lens, located between the contact member and image detector module, configured to substantially focus the image onto the image detector module; and a base station comprising an interface configured to couple the base station to the camera.

In some embodiments, the base station further comprises a data storage module that stores the outputted data of the acquired image. In some embodiments, the base station further comprises a microprocessor that controls base station functionality. In some embodiments, the base station further comprises a user interface, coupled to the microprocessor.

In some embodiments, the interface is configured to exchange data between the base station and the camera. In some embodiments, the interface is configured to provide power to the camera.

In some embodiments, the base station further comprises a display module. In some embodiments, the display module comprises at least one of a video display, an LCD display, an organic light-emitting diode (OLED) display, an LED, display, and a printer.

In some embodiments, the camera comprises an inductive coil to receive power inductively from a power source.

In some embodiments, the camera further comprises a network interface, said network interface configured to exchange data between the base station and at least one of the Internet, an intranet, a wide area network, a metropolitan area network, a local area network, a virtual private network, and a wireless network.

In some embodiments, there is provided a method, of observing a fundus of an eye in a patient, comprising: providing a compact fundus camera, the fundus camera comprising: a contact member, located at a distal end of the camera, configured to contact at least a portion of a cornea of the eye, and wherein the contact member is substantially transparent to light; an image detector module, located proximal the camera, configured to acquire an image of at least a portion of the fundus and to output at image data; an imaging lens, located between the contact member and image detector module, that substantially focuses an image of the ocular fundus on the image detector module; a power supply that provides power to the image detector module; contacting the cornea of the eye with the contact member; directing the image detector module to acquire a plurality of images of the fundus while the contact member is in contact with the cornea of the eye; and outputting the plurality of images to at least one image data file.

In some embodiments, a method, of observing a fundus of an eye in a patient, includes providing a compact fundus camera, the fundus camera having a camera housing; a contact member, located at a distal end of the camera, configured to contact at least a portion of a cornea of the eye, and wherein the contact member is substantially transparent to light; an image detector module, located proximal contact member, configured to acquire an image of at least a portion of the fundus of the eye and to output image data; an imaging lens, located between the contact member and image detector module, that substantially focuses an image of the fundus on the image detector module; wherein the image detector module and the imaging lens are coupled to the camera housing; and wherein at least one of the image detector module and the imaging lens is moveable substantially along an optical axis of the camera. In some embodiments, the method further includes contacting the cornea of the eye with the contact member; directing the image detector module to acquire a plurality of images of the fundus while the contact member is in contact with the cornea of the eye; and outputting the plurality of images to at least one image data file.

In some embodiments, the method further comprises illuminating at least a portion of the fundus of the eye with an illumination source. In some embodiments, the illumination source comprises an LED. In some embodiments, the illumination emits one of UV, visible, and infrared light.

In some embodiments, the image detector automatically acquires the plurality of images upon contact of the contact member with the cornea. In some embodiments, an operator manually directs the image detector to acquire the plurality of images.

In some embodiments, the method further comprises moving the imaging lens substantially along an optical axis of the fundus camera during acquisition of the plurality of images, such that at least one image of the fundus is substantially focused on the image detector module. In some embodiments, movement of the imaging lens occurs automatically.

In some embodiments, the method further comprises selecting an optimal image from the plurality of images. In some embodiments, the selecting is performed by imaging software.

In some embodiments, the method further comprises covering at least a portion of the contact member with a transparent coverlet. In some embodiments, the coverlet is substantially translucent.

In some embodiments, the method further comprises applying a topical anaesthetic to the patient's eye prior to contacting the cornea with the contact member.

In some embodiments, the method further comprises storing the image data in a memory portion of the camera. In some embodiments, the method further comprises outputting the image data from the camera to a peripheral device.

In some embodiments, the peripheral device comprises at least one of a computer, a personal data assistant, a portable telephone, and a base station.

In some embodiments, the method further comprises outputting the at least one image data file to a network. In some embodiments, the network comprises at least one of the Internet, an intranet, a wide area network, a metropolitan area network, a local area network, a virtual private network, and a wireless network.

In some embodiments, the peripheral device comprises a base station configured to be coupled with the camera.

In some embodiments, the method further comprises displaying the image data on a display module. In some embodiments, the display module comprises at least one a video display, an LCD display, and a printer.

In some embodiments, the method further comprises storing the image data in a memory portion of the base station.

In some embodiments, the method further comprises providing a camera having a rechargeable battery.

In some embodiments, coupling the camera and the base station results in at least one of recharging the rechargeable battery and exchanging data between the base station and the camera.

In some embodiments, a method, of observing a fundus of an eye in a patient, includes providing a compact fundus camera, the fundus camera having a camera housing with proximal and distal ends; a contact member, positioned at or distal to a distal end of the camera housing, a portion of the contact member being configured to contact at least a portion of a cornea of the eye, and wherein the contact member is substantially transmissive of light; an image detector module, located proximally with respect to the contact member, the image detector module being configured to acquire an image of at least a portion of the fundus of the eye and to output data indicative of the image; and an imaging lens, positioned between the contact member and the image detector module, the image lens directing the image to the image detector module. The image detector module and the imaging lens are coupled to the camera housing in some embodiments. In some embodiments, by moving at least one of the image detector module and the imaging lens, relative to the contact member, along an optical axis of the camera, acquiring a plurality of images of the fundus while the contact member is in contact with the cornea of the eye, each of the plurality of images being acquired by the image detector module having a different focus than each of the other of the plurality of images. The method further includes selecting from the plurality of images a selection image having an optimal focus relative to the others of the plurality of images and outputting the selection image to at least one image data file.

DETAILED DESCRIPTION OF THE INVENTION

Methods and apparatus available for performing examinations of the ocular fundus are either difficult to perform (e.g., ophthalmoscope) or involve expensive, non-portable pieces of equipment (e.g., commercially available fundus camera systems).

Embodiments of the present disclosure describe a compact ocular fundus camera that can be both easy to use and fully portable. In general terms, the camera will comprise at least a contact surface adapted to contact the cornea of a patient's eye, an illumination source to illuminate the fundus, an image detector that receives an image of the fundus from light reflected back from the eye and outputs an image data file, and an imaging lens, operative to focus light reflected back from the fundus onto the imaging surface of the image detector. The camera will also comprise communication capability, either wired or wireless to permit transmission of image data to at least one peripheral device. In some embodiments, the camera is simple and cheap to make and thus can be made to be disposable.

Figure 1A:
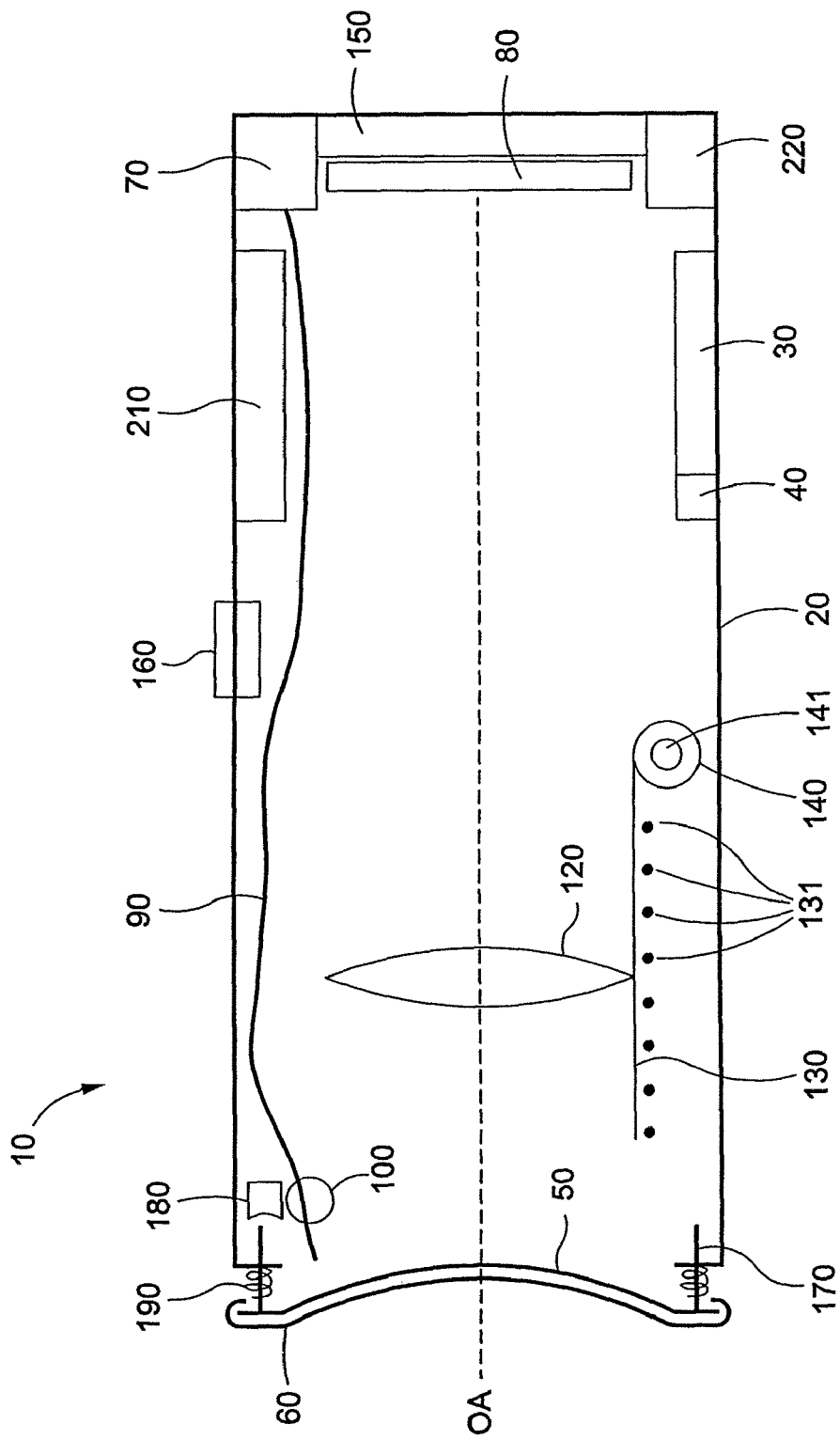
FIG. 1A illustrates a cross-sectional view of embodiments of a compact fundus camera.

In some embodiments, for example as illustrated in FIG. 1A, the fundus camera 10 includes a camera housing 20 that contains and protects the imaging components. The camera housing 20 can be fashioned of lightweight resilient materials. In some embodiments, the fundus camera 10 comprises a compact, handheld unit, approximately the size of a pen. In some embodiments, the device is about 24 mm×about 24 mm×about 125 mm, and weighs less than about 100 g. Conveniently, any fundus camera having a compact size and weight that would allow for easy handheld use will be suitable. Accordingly, the precise dimensions of the camera are not considered to be limiting to the scope of the present disclosure.

The compact fundus camera 10 includes a power supply 30. In some embodiments, the power supply 30 can be a disposable battery, for example, and without being limited, a 3V lithium battery. It will be appreciated that a number of batteries having a range of voltages will be useable, the choice of battery being dictated by the number of uses desired before the battery needs replacing and the load imposed by the various electronic circuits of the camera. In some embodiments, the camera will be able to perform about 200 eye exams before batteries need replacing.

In some cases, the power supply 30 can be a rechargeable battery. The power source for recharging can be a standard AC adaptor device that converts domestic current to a voltage suitable for charging the onboard battery. In some embodiments, a USB port on a computer could be operative as the power source to recharge the power supply 30. Conveniently, where a rechargeable battery is used, the camera can also include a plug 40, to connect the power source (not shown) to the battery. A rechargeable battery can be a NiCd, NiMH, or any other suitable rechargeable battery. In some embodiments, it can also be possible to charge the battery inductively, for example, as disclosed in U.S. Pat. No. 5,959,433 to Rohde, the entire contents of which are herein incorporated by reference.

It will be understood that all electronic components of the camera are electronically coupled to at least the power source (e.g., to the battery). In some cases, electronic components can be electronically coupled to both the battery and other components.

In some embodiments, the fundus camera 10 can be configured to comprise a contact member 50 located at a distal end of the camera. When using the camera 10, the contact member 50 is positioned so that it makes contact with the surface of the cornea. To provide the greatest contact area, and hence the best image quality, the portion of the contact member 50 that contacts the eye can be substantially concave, and can have a radius of curvature that is approximately equal to a radius of curvature of the cornea. As different patients can have differing corneal curvature, and thus different radii, the radius of curvature of the contact member can be within 10%, 20%, 30%, or any other suitable percentage of the radius of the curvature of the patient's eye that is to be imaged by the camera, and still provide useful images of the fundus. In some embodiments, the contact member can be substantially flat, such that pressing the contact member against the eye will provide a pathway for light reflected from the fundus to be transmitted to an image detector 80.

In some embodiments, the contact member 50 can comprise a flexible material, such that with a modest amount of pressure, the contact member 50 will deform and thus conform to the shape of the patient's cornea. In some embodiments, the contact member 50 is configured to have substantially the same refractive index as does the cornea of the human eye. In operation, the contact member 50 is effective to neutralize corneal refractive power (approx. 42 diopters).

The contact member 50 can be made to be disposable. In this case, before each exam, the user installs a new contact member 50 on the camera 10. A disposable contact member 50 can be provided in a sterile condition, which would avoid the need for cleaning of the contact member between each eye exam, and would in turn reduce the risk of eye infection by transmission of microbes or viruses from one patient to the next, or from one eye to the other of the same patient.

Alternatively, in some embodiments, the contact member 50 is permanently attached to the camera. In these embodiments, the contact member 50 can further comprise a replaceable coverlet 60. The coverlet 60 can be removed from one eye exam to the next to reduce the chances of spreading infection. Further, the coverlet 60 could be provided in sterile packaging as a one use item, again obviating the need to clean the contact surface from one exam to the next.

Further, where either a disposable contact member 50 or coverlet 60 are used, either could be provided as part of a kit including a plurality contact members 50 or coverlets 60 covering a range of curvatures. In preparation for an imaging procedure, the operator could first measure the patient's eye curvature using a standard ophthalmometer, and then select the closest matching contact member 50 or coverlet 60 to provide the best fit between the contact member 50 and the patient's eye.

The camera can further comprise an illumination source 70, effective to provide illumination of the ocular fundus. In some embodiments, illumination is provided by an LED, although the choice of illumination source is not limiting. In some embodiments, a number of LEDs can be provided, each of which emits in a different portion of the electromagnetic spectrum. For example, in some embodiments, LEDs are provided that can illuminate the fundus with light in the near UV, visible, or infra-red ranges of the electromagnetic spectrum, allowing different types of ocular analysis. For example, in some cases, fundus angiography can be performed using UV light in combination with fluorescein (Chen et al., *Clin. Exp. Ophthalmol.* 34: 600-605 (2006)), or infrared light in combination with indocyanine green (Brown et al., *Br. J. Ophthalmol.* 57: 797-802 (1973)).

One or more illumination source 70 can be oriented such that sufficient light is directed towards the fundus. In some embodiments, the illumination source will be partially shielded to reduce the amount of scattered light so that the image detector 80 is not "blinded" by the illumination source. In some embodiments, the illumination source(s) 70 can be completely contained, with light transmitted via an optical fiber 90, or fiber bundle. In this case, the emitting end of the optical fiber 90 could be conveniently positioned near the contact member 50 and oriented to provide effective illumination of the fundus. In addition, the end of the optical fiber could be further coupled to a moveable holder 100, such that the operator could change the angle of the optical fiber 90 in order to direct light to a particular portion of the fundus, if desired. In some embodiments, the optical fiber can comprise an optic fiber ring placed around the outer edge of the contact member 50.

Where the camera is provided with a number of illumination sources to provide illumination of various wavelengths, the camera can further comprise a mode selector to select between each illumination source. For example, as illustrated in FIG. 1B, a slide switch 110 located on the back of the camera housing, could be configured to allow the user to select between individual UV, visible, or infra-red emitting LEDs. Other configurations of mode selectors are also possible, for example, one that permits selection of two or more illumination sources simultaneously.

In some embodiments, the camera further comprises an imaging lens 120. The imaging lens 120 is effective to receive light reflected back from the fundus and to focus an image on an image detector 80. In some embodiments, the imaging lens 120 will be oriented such that its optical axis (OA) is generally aligned with the longitudinal axis of the camera. The optical axis will generally be oriented substantially perpendicular to the image plane of the image detector 80. In some embodiments, the optical axis may oriented in other ways, and so the precise optical path for light in the camera is not considered to limit the present disclosure.

In some embodiments the imaging lens 120 can comprise a single lens element with a power selected such that the image of the fundus is focused on the image detector 80. In some embodiments, the imaging lens 120 can comprise a multiple element lens in order to form a focused image having a wider field of view. In some embodiment a second imaging lens 121 can be provided in order to alter the optic characteristics of the camera, for example to provide magnification of the image, or a wider field of view, as depicted in FIG. 1D. In some embodiments, the second imaging lens can function as a collimating lens. In some embodiments, the second imaging lens can be made to be movable, for example, in order to vary magnification or field of view.

As has been indicated, embodiments of the camera can be provided where the imaging lens, the second imaging lens, and the image detector, are movable. In some embodiments, the imaging lens, the second imaging lens, and the image detector, are movable relative to each other and/or to the camera housing. Each of the imaging lens, the second imaging lens, and the image detector can be movable relative to each other, or as a group. Thus, in some embodiments, the imaging lens can move relative to the second imaging lens and/or the image detector. In some embodiments, the second imaging lens can move relative to the imaging lens and/or the image detector. In some embodiments, the image detector can move relative to the imaging lens and/or the second imaging lens.

For example, in eyepieces for astronomical instruments, a number of multi-element lens designs have been developed to improve the width of the field of view, while minimizing spherical aberration. Kellner, Ramsden, and Plossl, are exemplary lens configurations known in the astronomy arts to provide fields of view as wide as about 50°. In the fundus camera, similar optical designs can be used to collect light reflected from the fundus and form a wide field image on the image detector 80. All possible combinations of single, or multiple element lenses, are within the scope of the term "imaging lens," as the term is used herein. Elements of the imaging lens, and other light-transmitting members can further comprise non-glare, or non-reflective coatings in order to improve image quality and efficiency of light transmission.

Due to individual variation in eye structure and corneal and lens conformations, not all eyes have the same optical characteristics. Thus, the image reflected back from the fundus will not necessarily focus in the same plane from one eye to the next. Therefore, with a fixed imaging lens, the camera as a whole would have to be moved back and forth in order to focus an image of the fundus on the image detector. Accordingly, in some embodiments of the present disclosure, a further advantage is provided by having the imaging lens 120 be movable generally along an optical axis of the camera 10. Moving the imaging lens 120 along the optical axis will, at some point, result in an image of the fundus being focused on the image detector 80, regardless of the optical characteristics of the eye being examined.

A variety of mechanisms can be used to effectively move the imaging lens 120 with respect to the plane of the image detector 80. For example, and without limitation, tracks, gears, slides, and other devices can be effectively used to move the imaging lens back and forth with respect to the longitudinal axis of the camera. In some embodiments, the imaging lens 120 can be moved using a mechanism analogous to microscope or telescope focusers well known in the art, in which rotation of the focuser moves the imaging lens 120 with respect to the image detector 80. The focuser can be operated manually or automatically. In manually operated embodiments, a simple knob or other turning device can be used to move the imaging lens back and forth along a track or other like guide way.

In some embodiments, the imaging lens 120 is mounted on a track 130 that is moveable by a focusing drive 140. In some embodiments the focusing drive 140 is a manual control. In some embodiments, the focusing drive 140 is driven by electrical or mechanical energy and comprises a drive motor and gear, or other suitable combination to move the imaging lens back and forth along the optical axis of the camera.

Using a manually operated focuser, the imaging lens 120 can be easily moved by means of a knob or other turnable member coupled to a track 130, or other similar member on which the imaging lens can be mounted.

In one method of using a manually focusable embodiment, the camera image detector 80 is activated, and then the manual focuser mechanism is adjusted while the image detector acquires a number of images. As detectors are available that can acquire several images per second, a number of images can be acquired and then later analyzed for ones that provide the best imager quality. Image acquisition can be controlled in a number of ways. In some embodiments, a series of images can be acquired at preset time intervals, for example and without being limiting, at one image per second. The operator would move the imaging lens back and forth within the camera as images are taken.

In some embodiments, the camera can include a number of stops 131, or contact points, such as, for example, electrical contacts, configured to activate the image acquisition mode as the imaging lens is moved back and forth within the camera housing. For example, stops 131 can be placed at preset locations along the length of a track 130 to which the imaging lens is coupled. As the imaging lens passes each stop 131, a mechanical, electrical, or electromechanical device would trigger acquisition of an image. Moving the lens 120 past a number of stops 131, would thus result in a series of images being acquired. Again, movement of the imaging lens 120 can be accomplished manually or automatically.

In some embodiment, movement of the imaging lens can be accomplished in a controlled fashion through a movement regulator 141. The movement regulator 141 can be configured to move the imaging lens in a controlled continuous motion, in discrete steps, or in a combination of continuous and discrete movement. The movement regulator 141 can comprise a variety of mechanical, electrical, or electromechanical devices including without limitation, mechanisms with ratchets or detents, solenoids, spring driven or electrical driven gear combinations. In some embodiments, the movement regulator 141 can include dampers that restrict or limit the speed of the imaging lens 120. For example, in some embodiments, the imaging lens 120 is moved along the optical axis of the camera by releasing potential energy stored in a compacted or wound spring. Movement of the imaging lens 120 within the camera can be slowed by including dampers that provide a resistive force, such as friction, that resists movement of the imaging lens 120. In some embodiments, activation of the camera activates the movement regulator 141 to move the imaging lens along the optical axis of the camera. Concurrently, the image detector 80 can be activate to begin acquiring images as the imaging lens is moving. Thus, in the time required for the imaging lens to travel a distance along the optical axis, a series of images can be acquired.

In some embodiments, the camera can include a plurality of lenses that are configured to adjust and prepare the image for the image detector 80. For example, in some embodiments, a first lens is positioned at the distal end of the camera at a position near or adjacent the contact member 50, and a second lens can be positioned at a location proximal the first lens. For example, the second lens can be the imaging lens 120, discussed in embodiments herein, and be capable of movement with respect to both the first lens at the distal end of the camera and the image detector 80. In some embodiments, the first lens can be movable with respect to the other lens and/or the image detector 80.

In an exemplary embodiment, the movement regulator 141 is configured to move the imaging lens 120 along a predetermined track in a time of about 2 sec. During this time the image detector 80 acquires a plurality of images. In some image detectors, at least 20 images can be taken in the course of about 1-2 sec. The images can be saved in memory within the camera and downloaded later to a peripheral device for analysis or image selection, or the images can be transmitted in real-time to a peripheral device.

The peripheral device can be used to review a series of images for an optimal image. In some embodiments, this review can be performed manually, and in some embodiments, the peripheral device will further comprise software that automatically selects the optimum image from an image series.

Figure 2:
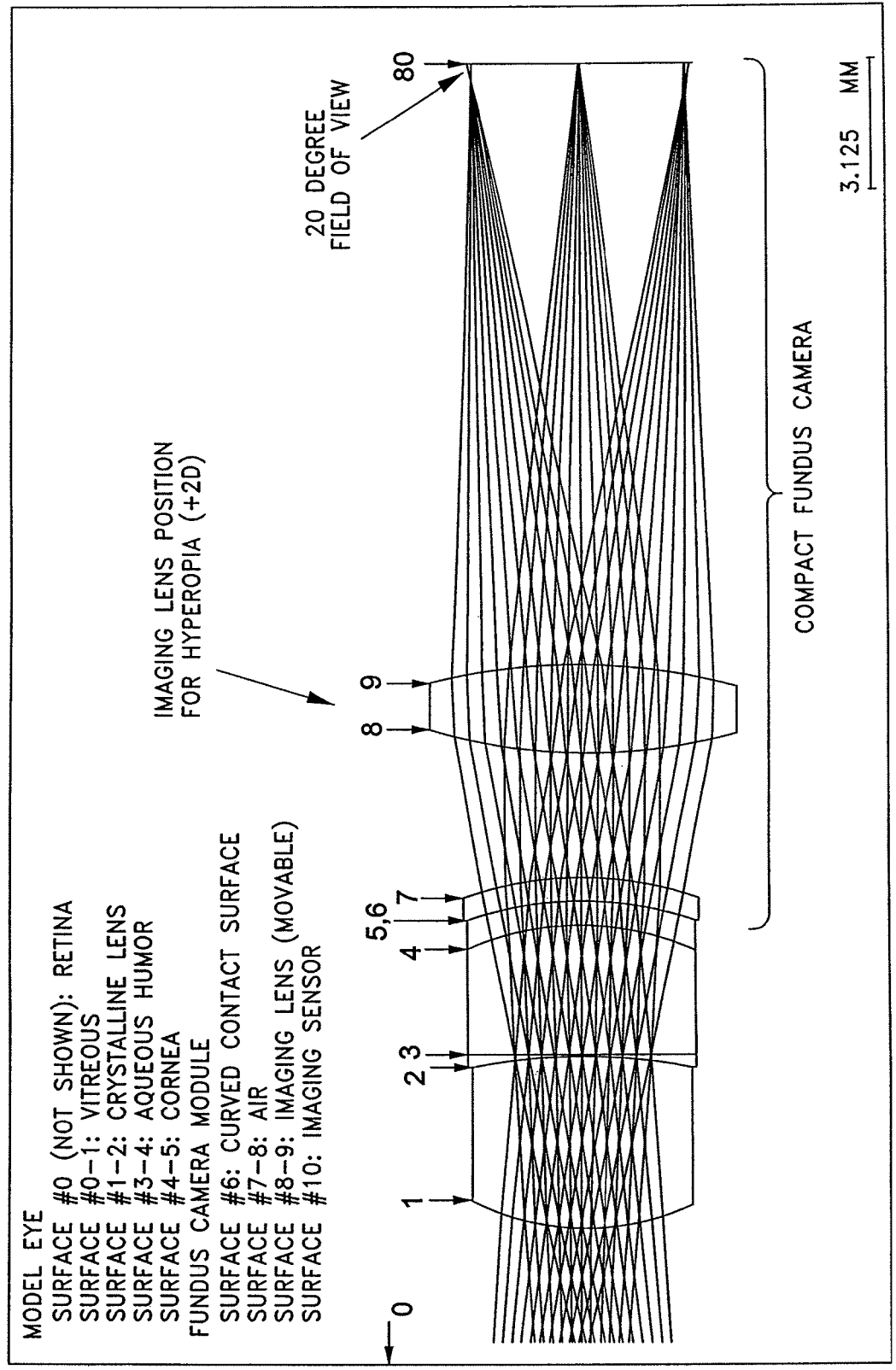
FIG. 2 illustrates embodiments of an compact fundus camera with an imaging lens positioned for hyperopia.
Figure 3:
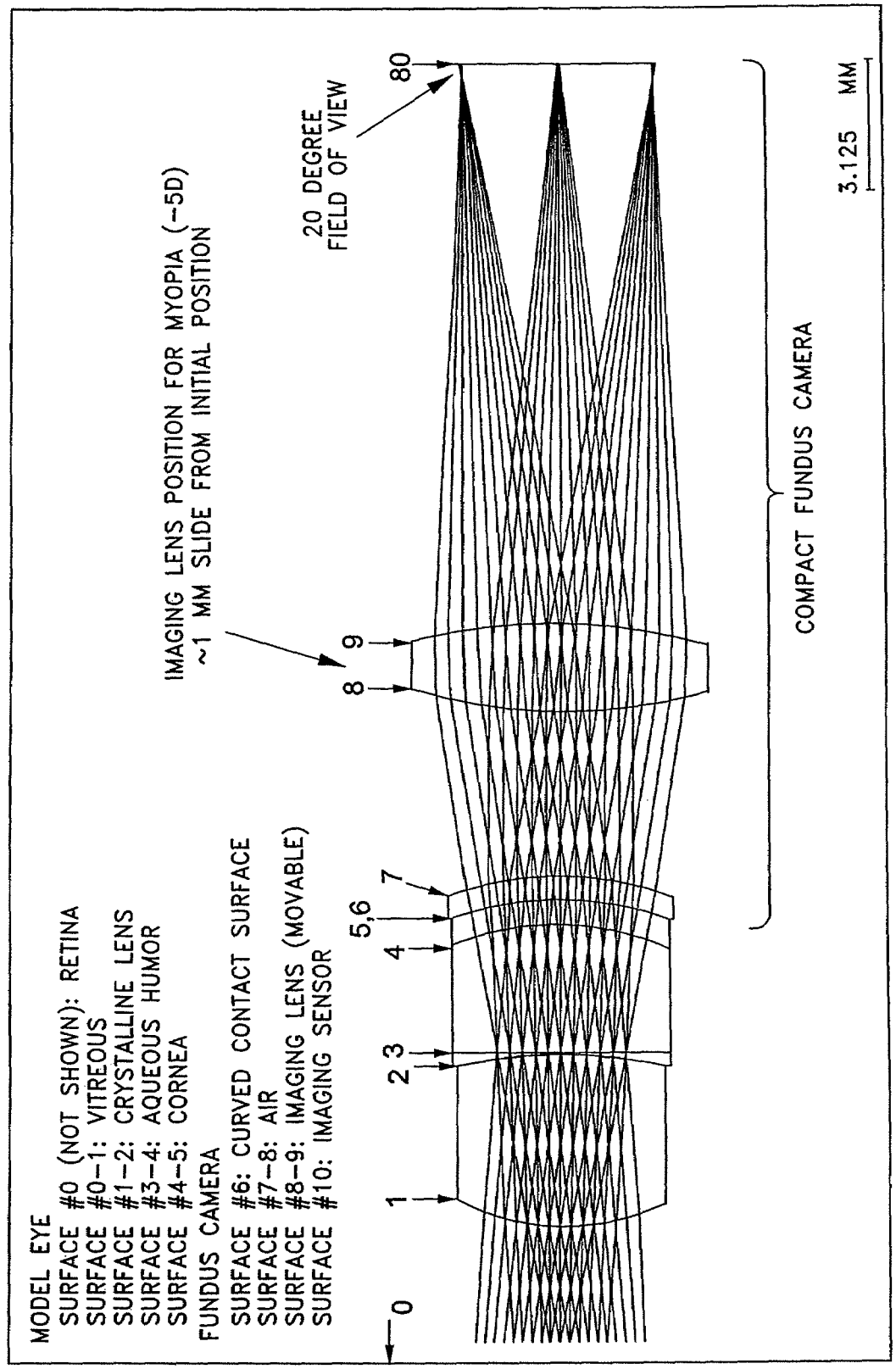
FIG. 3 illustrates embodiments of an compact fundus camera with an imaging lens positioned for myopia.

With an automatically operated focuser, a motor drive can be used to move the imaging lens 120 back and forth along the optical axis of the camera 10. Upon contact with the patient's eye and activation of the image detector, the automatic focuser will move the imaging lens 120 while the image detector 80 acquires images. For example, the illustrations show exemplary imaging lens positions for imaging a hyperopic eye (FIG. 2) or a myopic eye (FIG. 3).

As before, the images can be later reviewed to select those that provide the best diagnostic information and/or which are in the best focus, allowing for selection of one or more "optimal" images. In either the manual or automatic focusing embodiments, there can also be included software that automatically selects an optimal image from a sequence of images.

Figure 1C:
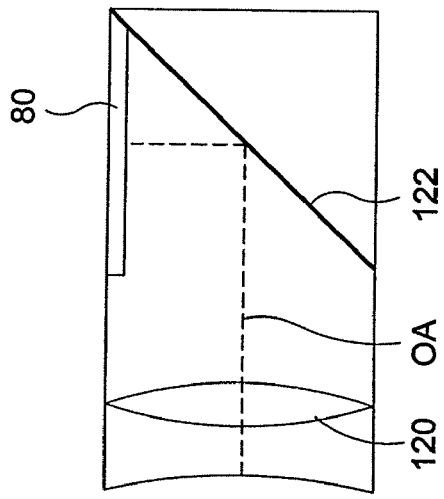
FIG. 1C illustrates embodiments of a compact fundus camera with an imaging lens and a reflective mirror.
Figure 1D:
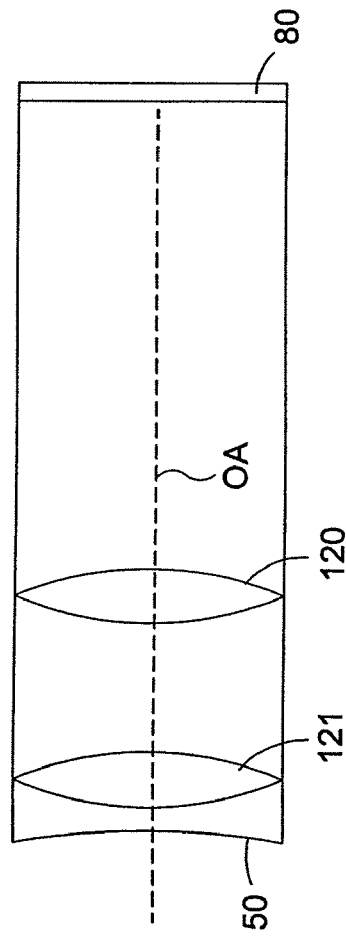
FIG. 1D illustrates embodiments of a compact fundus camera with a second imaging lens.
Figure 1B:
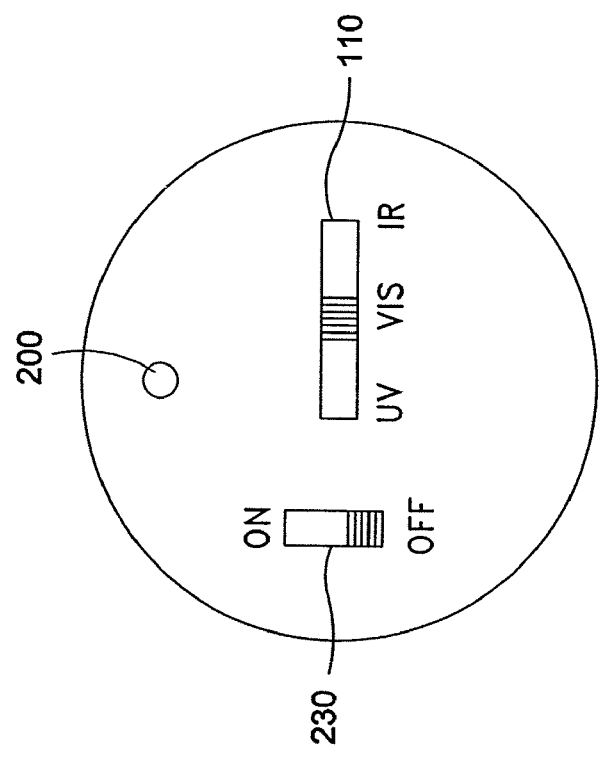
FIG. 1B illustrates embodiments of a compact fundus camera showing an exemplary configuration of control switches and indicators.

In some embodiments, the imaging lens 120 can include a reflective mirror 122 that is configured to direct reflected light from the fundus toward the image detector 80, as depicted in FIG. 1C. For example, in some embodiments, the image detector 80 can be oriented such that it is not in direct view, or along a single axis, of the acquired image. The imaging lens 120 can be configured to deflect the acquired image toward the image detector 80. In some instances, the imaging lens 120 can be configured to rotate as it moves in order to direct the acquired image toward the image detector 80.

In some embodiments, the imaging lens 120 can be in a fixed position, and the image detector 80 can be moved with respect to the imaging lens during image acquisition. For example, the image detector 80 can be configured to be coupled to the track 130 that is moveable by the focusing drive 140. The track 130 with the image detector 80 can be activated in a similar fashion as discussed in this disclosure with respect to other embodiments, and can be driven by electrical, mechanical, hydraulics and can include a drive motor and gear, or other suitable combination to move the imaging lens back and forth along the optical axis of the camera. In some embodiments, the camera can comprise an auto-focus mechanism, such as that described in U.S. Pat. No. 7,046,290 to Nozaki, herein incorporated by reference in its entirety. In some embodiments that include an auto focuser, the camera could automatically determine the best position of the imaging lens in order to form a focused image on the image detector, and the camera could then automatically store the image. This would reduce the amount of time and data storage needed to obtain an optimal image.

The image detector 80 receives light reflected from the fundus and converts it into a useable form, in some embodiments a digital image data file. In some embodiments, the signal from the image detector 80 can be used to directly drive a display module, for example and without being limiting, an LCD or like display. The image detector 80 can be a CMOS chip, a CCD chip or any other suitable light-sensing device. In some embodiments, the image detector comprises a 2048× 2048 array of pixel elements. In some embodiments, larger arrays can be used. In a camera with a field of view of 50°, an array of at least 3000×3000 pixels will provide an image with 60 pixels per degree of arc. Where a CCD, CMOS, or other digital output device is used, the images can be stored or transmitted as digital data. Depending on the detector used, images can be in color, levels of gray, false color, or any other suitable format.

In some embodiments, the image detector is coupled to a control module 150 that is configured to control the acquisition of images by the image detector 80, or other aspects of image detector function such as frame rate, or contrast and brightness, etc. The control module 150 can also be adapted for use in image processing or sorting, for example for sorting image data files according to acceptable brightness, contrast, focus, or any other desirable image parameter desired in the outputted image. In some embodiments, the control module 150 comprises a microprocessor, or like device, that can be programmed either in software or firmware to control the operation of the image detector as well as other features of the camera, including, without limitation, operations of the imaging lens mechanism, the illumination source, data input and output capabilities, and image processing.

Positioning the camera for image acquisition is relatively simple. Prior to imaging, a topical anaesthetic drop (e.g., proparicaine) can be applied to the patient's eye. The contact member is pressed gently against the patient's cornea, the camera oriented so that the optical axis of the camera will be in approximate alignment with the optical axis of the eye. Perfect alignment is not required, and suitable images can be obtained even if the two optical axes are not in perfect alignment.

Once the camera is positioned, at least one digital image can be captured by activating the image acquisition capability of the camera. Image acquisition can be activated manually, for example by the user pressing a button 160 mounted on the camera body that is coupled to circuitry controlling the capture of images by the image detector, much like pressing the shutter button on a traditional digital camera.

In some embodiments, activating the image acquisition capability can be done automatically upon contacting the cornea with the contact member 50. In this case, the contact member 50 can be movable along a track 170 or other similar mounting mechanism, such that pressing the camera against the cornea results in movement the contact member back towards to the proximal end of the camera (i.e., towards the image detector) or vice versa. In some embodiments, the contact member 50 can be further coupled to a micro switch 180 or other suitable switching device, such that when a pre-determined pressure is exerted, the micro switch closes a circuit that activates the image acquisition mode. Automating image acquisition allows the user to devote more attention to proper placement of the camera on the eye, and reduces the chance of moving the camera while activating a button or other control.

A bias force can be provided by the micro switch or other bias member 190, such that when the camera is pulled away from the surface of the eye the contact member is moved outward, the micro switch reverts to the open circuit configuration, and the image acquisition mode ends. The camera could either power off at this point, or perform other functions, such as data download or image display. These functions could be operated manually at the direction of the operator, or automatically as part of a pre-programmed sequence of events.

In some embodiments, when in image acquisition mode, a series of images are taken, either simultaneous to, or coordinated with, movement of the imaging lens along the optical axis of the camera. Whether the imaging lens is moved manually or automatically, movement of the imaging lens during acquisition of a series of images increases the likelihood that at least one image of the series will be focused well enough for diagnostic use. Whether in manual or automatic mode, the movement of the imaging lens can also be coordinated with image capture, such that an image is captured as the imaging lens is moved a predefined distance. Stops or detents along the imaging lens track 130, can also be used provide predefined position references that could be used to trigger acquisition of the next image in a series.

The camera can further comprise indicators 200, such as visual or audible alerts to let the user know when the camera is acquiring images. For example an LED located in a easily seen location on the housing of the camera could illuminate when image capture is taking place, and a transducer can emit a tone once image acquisition is complete, as shown in FIG. 1B. Combinations of visual and audible alerts can also be used. The camera can also include a manual on-off switch 230 to power off the camera when not in use.

In some embodiments, once images are captured they can be stored in a memory module 210 located within the camera for later use. In some embodiments, upon acquisition, images can be transmitted to an electronic device peripheral to the camera. This peripheral device can comprise, without limitation, a personal computer, a laptop computer, a handheld device (e.g., personal digital assistant), a wireless telephone with image or emailing capability, and the like.

Where images are transmitted to a peripheral device, transmission can be via a connecting cable, or wirelessly. Where a cable is used, the cable can be configured to be removable from the camera to make handling the camera during image acquisition more facile. After images are taken, a cable can be used to link the camera and the peripheral device, and the images stored in memory downloaded from the camera. Any of a number of data transmission formats can be used, including, without limitation, USB 1.0, USB 2.0, Firewire, Ethernet, and other analogous data transfer formats. It will be understood that the memory module 210, control module 150, and any output modules will be electronically coupled to each other such that data can be moved from one location to another, such as from the camera to a peripheral device.

Images can be produced and stored in a number of digital imaging formats including, without limitation, jpeg, tiff, bmp, gif, or other formats. Images can be stored as compressed or uncompressed image files.

Where wireless transmission is used, the camera can comprise a wireless transceiver 220 that operates via RF signals, or optical, electro-optical, electromagnetic, or any other wireless communication methods. The transceiver 220 could further communicate with devices that have email or other wireless networking capabilities (e.g., Blackberry and like devices) such that images could be downloaded from the camera to the networking device, and then relayed via email or other network data transfer means to another location or user. This would allow, for example, testing of patients in relatively remote locations where eye specialists may not be available, and then forwarding the images electronically to a qualified eye care professional for evaluation.

Figure 4:
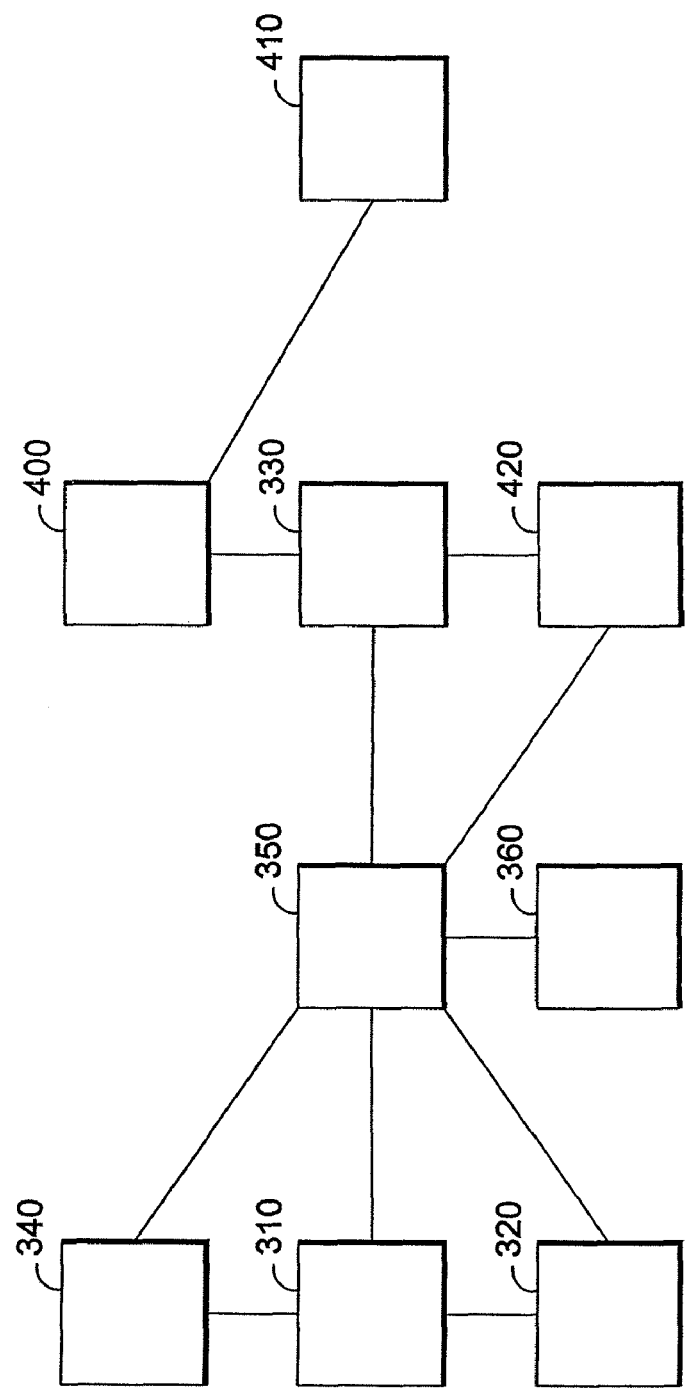
FIG. 4 illustrates a schematic view of embodiments of a compact fundus camera base station and associated components.

In some embodiments, the compact fundus camera can be provided along with a compatible base unit 300, as shown in FIG. 4. The base unit 300 can also be battery powered, or alternatively can utilize domestic AC current. Where the base unit is battery powered, the batteries can either be replaceable or rechargeable. The base station can be made small enough to also be portable.

The base unit 300 can include a display 310 such that images acquired by the camera can be transmitted to the base unit for display on a screen, for example and without being limiting, an LCD or OLED screen. The base unit 300 can also include, or be configured to direct, a printer 320 to print out images acquired from the camera, or stored previously in the base unit in a memory module. The printer can be an inkjet printer, laser printer, thermal printer or any other suitable printing device. In some embodiments, the printer can print the images on photographic quality printing paper, or any other suitable media.

The base unit 300 could also be configured to display images as they are being captured by the camera. In this "live" display mode, the camera could transmit images to the base unit as they are acquired and the base unit could in turn display the images on the display 310. This could provide a live action view of the fundus, allowing the eye professional to do exploratory investigation much like one would use an ophthalmoscope, except with greater ease and the ability to record data as it is acquired, something not possible with the traditional ophthalmoscope. With a frame capture rate greater than 24 fps, the camera could provide a smooth motion picture-like capability. Transmission of images from the camera to the base station can be either through a communications cable, or wirelessly. The base unit can comprise a communications network interface 330 that can allow the base unit 300 to communicate with a communications network, or alternatively with the fundus camera.

The base unit 300 can be further configured to transmit images to other computing devices and/or digital storage devices over a communications network 400 (e.g., the Internet, an intranet, local area networks, metropolitan area networks, wide area networks, virtual private networks, wireless network, and any other suitable network or combinations of network thereof). The images can be compressed using any suitable data compression or image compression algorithm prior to transmission over a network.

In some embodiments, the base unit is configured to store digital images in a digital storage module 340. These images can be received over a wireless network from the compact fundus camera, or could be received by the base unit from a communications network as described above. The base station 300 can digitally store the images in semiconductor memory, magnetic media, electromagnetic media, optical media, electro-optic media, or any other suitable media or combinations thereof. The base unit likewise can send images received from a camera out over a communications network 400 to other peripheral computing devices 410, or directly from the microprocessor to a coupled peripheral device 420.

In some embodiments, the base station can be configured to have a dwell station interface 350 for the handheld compact fundus camera. The dwell station interface 350 can provide data exchange capability between the camera and base unit for downloading images from the camera or for uploading programming instructions from the base unit to the control module of the camera. The interface can also be used to provide power for recharging the camera in embodiments of the camera that include a rechargeable battery. Conveniently, the plug 40 on the camera can be configured to provide both power and data interface capability.

Images downloaded to the base unit can be processed or sorted. The processed or sorted images can be stored in a memory device, for example a DRAM, flash memory, or any other suitable memory storage device, for post-acquisition transmission over a communications network or for any other analysis. Image processing algorithms can be applied to at least one of the acquired images to identify the best focused image.

The base unit can further comprise a central processing unit 350 for managing data transfer and the functionality of various functional components, as well as a user interface 360. The user interface 360 can comprise, for example and without limitation, a keyboard, touch screen or other suitable interface. The user interface 360 can be used to manipulate images (e.g., sort, annotate, save, delete, etc.). Personal, patient code, demographic, or any other suitable information related to the images can also be inputted using the user interface 360.

In a method of imaging a fundus of an eye using the compact fundus camera, proparicaine drops or any other suitable anesthetics are instilled in the conjuctival sac of the eye to be imaged. A protective coverlet can be placed on the fundus camera to prevent contamination of the subject's cornea. Alternatively, in embodiments where the contact member is disposable, a new contact member can be installed. Depending on the embodiment, either the coverlet, the contact member, or both can be provided in sterile packaging. In some embodiments, the camera operator may predetermine the radius of curvature of the patient's eye and then select a contact member or coverlet that best matches that curvature from a kit that includes coverlets or contact members covering a range of curvatures. The camera operator then positions the camera such that the camera is in contact with the eye.

Next, the operator presses an activation button to begin imaging the patient's fundus. As mentioned above, this activation button can be on the housing of the fundus camera or this activation button can be on a separate device, which sends instructions to the camera to begin the imaging process. These instructions to the camera can be communicated through a direct connection or wirelessly. An audio or visual cue, can be used to indicate to the operator that the camera is imaging the patient's fundus. In some embodiments, the camera will activate automatically once sufficient pressure is exerted on the cornea by the contact member, via activation of a micro switch.

In some embodiments, an operator can select imaging mode options to facilitate imaging of the fundus. These options can include settings for imaging long eye, short eye, or any other suitable options. During the imaging process, the subject is informed by the operator to look straight ahead or toward a point target. The handheld fundus camera is progressively applanated to the patient's cornea, providing 3-D range-finding in a nearly emmetropic eye.

The fundus camera acquires sequential images of the patient's fundus as the imaging lens is moved. From the images collected, at least one image is selected as optimal, and is stored or otherwise identified. What comprises an optimal image could be defined based on factors such as best focus, widest field of view, best view of multiple fundus structures, for example, retinal vessels, macula, optical disk, or any other suitable feature, and so what constitutes an optimal image will be at the discretion of the operator or eye care professional reviewing the images. Once determined, the optimal image can be transferred to a base station, either by a wired or wireless connection. The image can be displayed on the base station display, and options for annotation, printing, storage, or transfer are executed by the operator. These procedures, can be repeated for the contralateral eye if necessary.

A method of imaging can also include taking two images of the same eye that are off axis from each other. Taking two images at different angle permits stereo imaging of the fundus. This technique can be useful in detecting conditions such as macular edema.

The skilled artisan will recognize the interchangeability of various features from different embodiments. Similarly, the various features and steps discussed above, as well as other known equivalents for each such feature or step, can be mixed and matched by one of ordinary skill in this art to perform compositions or methods in accordance with principles described herein. Although the disclosure has been provided in the context of certain embodiments and examples, it will be understood by those skilled in the art that the disclosure extends beyond the specifically described embodiments to other alternative embodiments and/or uses and obvious modifications and equivalents thereof. Accordingly, the disclosure is not intended to be limited by the specific disclosures of embodiments herein.

What is claimed is:

1. A compact ocular fundus camera system, for imaging at least a portion of a fundus of an eye, comprising:
    a camera comprising:
    a camera housing having proximal and distal ends;
    a contact member, positioned at or distal to a distal end of the camera housing, a portion of the contact member being configured to contact at least a portion of a cornea of the eye, and wherein the contact member is substantially transmissive of light;
    an image detector module, located proximally with respect to the contact member, the image detector module being configured to acquire an image of at least a portion of the fundus and to output data indicative of the image; and
    an imaging lens, positioned between the contact member and the image detector module, the image lens directing the image to the image detector module;
    wherein the image detector module and the imaging lens are coupled to the camera housing;
    wherein at least one of the image detector module and the imaging lens is movable substantially along an optical axis of the camera; and
    wherein the image detector module is configured to acquire a plurality of images of the fundus as the at least one of the image detector module and the imaging lens is moved along the optical axis of the camera from a first position to a second position, each of the plurality of images corresponding to a predetermined location of the at least one of the image detector module and the imaging lens along the optical axis between the first position and the second position, wherein the predetermined locations are independent of information acquired from the eye being imaged.

2. The camera system of claim 1, wherein at least one of the image detector module and the imaging lens is moved within the camera housing by at least one of a release of potential energy that is stored in a biasing member coupled to the camera housing, electromagnetic energy, and a manually applied force.

3. The camera system of claim 2, wherein the manually applied force is transferred by an operator to at least one of the image detector module and the imaging lens by a lever extending outside the camera housing.

4. The camera system of claim 1, wherein at least one of the image detector module and the imaging lens is moved within the camera housing by a release of potential energy that is stored in a biasing member coupled to the camera housing, and
    further comprising an operator-activated switch configured to release least a portion of the potential energy.

5. The camera system of claim 1, further comprising a plurality of contact points, and wherein the image detector module is configured to acquire the plurality of images based on a relative position of the plurality of contact points with respect to at least one of the image detector module and the imaging lens.

6. The camera system of claim 1, wherein the imaging lens is movable with respect to the image detector module.

7. The camera system of claim 1, wherein the imaging lens is movable with respect to the contact member.

8. The camera system of claim 1, wherein the image detector module is movable with respect to the contact member.

9. The camera system of claim 1, wherein the camera housing is elongate and is less than about 15 cm in its longest dimension.

10. The camera system of claim 1, wherein the camera housing is elongate and is less than about 10 cm in its longest dimension.

11. The camera system of claim 1, further comprising a base station that exchanges data with the camera and stores the outputted data indicative of the image.

12. The camera system of claim 11, further comprising a network interface, said network interface configured to exchange data between the base station and at least one of the Internet, an intranet, a wide area network, a metropolitan area network, a local area network, a virtual private network, and a wireless network.

13. The camera system of claim 1, wherein the portion of the contact member that contacts the cornea comprises a substantially concave portion.

14. The camera system of claim 13, wherein the concave portion of the contact member has a radius of curvature that matches a radius of curvature of the cornea within a range of error from about 0% to about 30%.

15. The camera system of claim 1, wherein the contact member is configured to conform substantially to an anterior surface of the cornea when the contact member contacts the cornea.

16. The camera system of claim 1, wherein the contact member has a refractive index substantially equal to that of a cornea.

17. The camera system of claim 1, further comprising at least one illumination source coupled to the camera that emits at least one of ultra-violet, visible, and infrared light.

18. The camera system of claim 1, further comprising a data transmission module that exchanges information between the camera and at least one device peripheral to the camera, wherein the data transmission module further comprises at least one of a data transmission cable and a wireless transceiver.

19. The camera system of claim 1, wherein the contact member is movable, and the image detector module is configured to automatically acquire the plurality of images of the fundus when pressure applied to the contact member from the cornea causes the contact member to move proximally.

20. The camera system of claim 1, further comprising a plurality of triggers, wherein each of the plurality of triggers corresponds to one of the different locations along the optical axis and each of the plurality of triggers is configured to trigger the image detector module to acquire one of the plurality of images when one of the image detector module and imaging lens passes the corresponding location.

21. The camera system of claim 20, wherein the plurality of triggers comprises a plurality of contact points.

22. A method, of observing a fundus of an eye in a patient, comprising:
    providing a compact fundus camera, the fundus camera comprising:
    a camera housing;

a contact member, located at a distal end of the camera, configured to contact at least a portion of a cornea of the eye, and wherein the contact member is substantially transparent to light;

an image detector module, located proximal the contact member, configured to acquire an image of at least a portion of the fundus of the eye and to output image data;

an imaging lens, located between the contact member and image detector module, that substantially focuses an image of the fundus on the image detector module;

wherein the image detector module and the imaging lens are coupled to the camera housing; and wherein at least one of the image detector module and the imaging lens is moveable substantially along an optical axis of the camera;

contacting the cornea of the eye with the contact member;

moving the at least one of the image detector module and the imaging lens along the optical axis of the camera from a first position to a second position;

directing the image detector module to acquire a plurality of images of the fundus while the contact member is in contact with the cornea of the eye, while the at least one of the image detector module and the imaging lens is moved, and when the at least one of the image detector module and the imaging lens is at predetermined locations between the first position and second position wherein the predetermined locations are independent of information acquired from the eye being imaged; and outputting the plurality of images to at least one image data file.

23. The method of claim 22, wherein the image detector module automatically acquires the plurality of images upon contact of the contact member with the cornea.

24. The method of claim 22, further comprising moving at least one of the image detector module and the imaging lens substantially along an optical axis of the fundus camera during acquisition of the plurality of images.

25. The method of claim 22, further comprising covering at least a portion of the contact member with a substantially translucent coverlet.

26. The method of claim 22, further comprising illuminating at least a portion of the fundus of the eye with an illumination source.

27. The method of claim 26, wherein the illumination source comprises an LED.

28. The method of claim 26, wherein the illumination emits one of UV, visible, and infrared light.

29. A method, of observing a fundus of an eye in a patient, comprising:

providing a compact fundus camera, the fundus camera comprising:

a camera housing having proximal and distal ends;

a contact member, positioned at or distal to a distal end of the camera housing, a portion of the contact member being configured to contact at least a portion of a cornea of the eye, and wherein the contact member is substantially transmissive of light;

an image detector module, located proximally with respect to the contact member, the image detector module being configured to acquire an image of at least a portion of the fundus of the eye and to output data indicative of the image; and an imaging lens, positioned between the contact member and the image detector module, the image lens directing the image to the image detector module;

wherein the image detector module and the imaging lens are coupled to the camera housing; and by moving at least one of the image detector module and the imaging lens from a first point to a second point, relative to the contact member, along an optical axis of the camera, acquiring a plurality of images of the fundus as the at least one of the image detector module and the imaging lens is moved along the optical axis from the first point to the second point, each of the plurality of images corresponding to a different predetermined location along the optical axis, wherein the predetermined locations are independent of information acquired from the eye being imaged; and selecting from the plurality of images a selection image having an optimal focus relative to the others of the plurality of images and outputting the selection image to at least one image data file.

30. A compact ocular fundus camera system, for imaging at least a portion of a fundus of an eye, comprising:

a camera comprising:

a camera housing having proximal and distal ends;

a contact member, positioned at or distal to a distal end of the camera housing, a portion of the contact member being configured to contact at least a portion of a cornea of the eye, and wherein the contact member is substantially transmissive of light;

an image detector module, located proximally with respect to the contact member, the image detector module being configured to acquire an image of at least a portion of the fundus and to output data indicative of the image;

an imaging lens, positioned between the contact member and the image detector module, the image lens directing the image to the image detector module, wherein the image detector module and the imaging lens are coupled to the camera housing and at least one of the image detector module and the imaging lens is movable substantially along an optical axis of the camera; and a plurality of physical triggers within the camera housing and disposed along a length of the camera housing, wherein each of the plurality of physical triggers corresponds to a different predetermined location along the optical axis and each of the plurality of physical triggers is configured to trigger the image detector module to acquire one of the plurality of images when one of the image detector module and imaging lens passes the corresponding predetermined location.

* * * * *